US00PP15383P2

(12) United States Plant Patent
Olesen et al.

(10) Patent No.: US PP15,383 P2
(45) Date of Patent: Nov. 30, 2004

(54) ROSE PLANT NAMED 'POULPM002'

(50) Latin Name: *Rosa hybrid*
Varietal Denomination: POULpm002

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,742

(22) Filed: Mar. 29, 2004

(51) Int. Cl.[7] ..... A01H 5/00
(52) U.S. Cl. ..... Plt./137
(58) Field of Search ..... Plt./137

*Primary Examiner*—Anne Marie Grunberg
*Assistant Examiner*—Annette H Para

(57) ABSTRACT

A new garden rose plant of the hybrid tea class which has abundant, pink flowers and attractive foliage. This new and distinct variety has shown to be uniform and stable in the resulting generations from asexual propagation.

1 Drawing Sheet

Botanical classification: *Rosa hybrid.*
Variety denomination: 'POULpm002'.

SUMMARY OF THE INVENTION

The present invention constitutes a new and distinct variety of garden rose plant which originated from a controlled crossing between the female seed parent, an unnamed seedling, and the male pollen parent 'Macrexy', described and illustrated in U.S. Plant Pat. No. 6,713 dated Apr. 4, 1989. The two parents were crossed during the summer of 1989 and the resulting seeds were planted in a controlled environment in Fredensborg, Denmark. The new variety is named 'POULpm002'.

The new variety may be distinguished from its female seed parent by the following combination of characteristics:

1. The seed parent has near white flower petals, while 'POULpm002' has pink flower petals.
2. The seed parent has a taller growth habit than 'Poulpm002'.

The new variety may be distinguished from its male pollen parent, 'MACrexy' by the following combination of characteristics:

1. Flowers of 'MACrexy' have 39 to 51 petals while flowers of 'Poulpm002' have 26 to 30 petals.
2. While the outer surface of flower petals of 'MAXrexy' are Red 55A to Red 56D in color, the outer surface of petals for 'Poulpm002' is Red-Purple Group 63C.

The objective of the hybridization of this rose variety was to create a new and distinct variety for garden use with unique qualities, such as:

1. Uniform and abundant pink flowers;
2. Dense, uniform growth habit;
3. Disease resistance.

This combination of qualities is not present in previously available commercial cultivars of this type, known to the inventors, and distinguish 'POULpm002' from all other varieties of which we are aware.

As part of their rose development program, L. Pernille Olesen and Mogens N. Olesen germinated the seeds from the aforementioned hybridization during winter of 1989 and conducted evaluations on the resulting seedlings in a controlled environment in Fredensborg, Denmark.

'POULpm002' was selected in the spring 1990 by the inventors as a single plant from the progeny of the aforementioned hybridization.

Asexual reproduction of 'POULpm002' by traditional budding and rooted cuttings was first done by L. Pernille and Mogens N. Olesen in their nursery in Fredensborg, Denmark in July, 1990. This initial and other subsequent asexual propagations conducted in controlled environments have demonstrated that the characteristics of 'POULpm002' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULpm002'. Specifically illustrated in the drawing:

FIG. 1.1; Open flower, stem showing open flower, branching, and the attachment of leaves, buds, and peduncles;

FIG. 1.2; Flower bud as sepals unfold;

FIG. 1.3; Sepals, receptacle, and peduncle;

FIG. 1.4; Flower petals, detached;

FIG. 1.5; Mature and juvenile leaf;

FIG. 1.6; Juvenile growth exhibiting anthocyanin;

FIG. 1.7; Juvenile and mature stems.

DETAILED DESCRIPTION OF THE VARIETY

The following is a description of 'POULpm002', as observed in its growth in a field nursery in Jackson County, Oreg. Observed plants are 3 years of age and were grown on *Rosa multiflora* understock. Color references are made using The Royal Horticultural Society (London, England) Colour Chart, 1995, except where common terms of color are used.

For a comparison, several physical characteristics of the rose variety 'TANalapin', described and illustrated in U.S. Plant Pat. No. 14,091 issued Aug. 26, 2003 are compared to 'POULpm002' in Chart 1.

CHART 1

| | 'POULpm002' | 'TANalapin' |
|---|---|---|
| Petal color: upper surface | Red Group 55B | Red Group 55A |
| Petal spot | Yellow Group 2B to 2C | White Group 49D |
| Petalage | 26 to 30 petals | 30 petals |

FLOWER and FLOWER BUD

Blooming habit: Recurrent.

Flower bud:

*Size.*—Upon opening, 23 mm in length from base of receptacle to end of bud. Bud diameter is 15 mm.

*Bud form.*—Pointed ovoid, broad based.

*Bud color.*—As sepals unfold, petals are Red Group 43C. Red Group 43C with intonations of Red Group 43B to 46A at ¼ opening.

*Sepals.*—Upper Surface: Color: Yellow-Green Group 145B. Surface: Moderately pubescent. Lower Surface: Color: Yellow-Green Group 144B. Anthocyanic pigments the color of Greyed-Red Group 180A observed. Texture: Rough with abundant stipitate glands. Sepal Shape: Sepal apex is cirrhose. Base is flat at union with receptacle. Sepal Margin: Margins have strong foliaceous appendages on three of the five sepals. Size: 22 mm long by 7 mm wide.

*Receptacle.*—Surface Texture: Smooth. Shape: Funnel shaped. Size: 9 mm (h)×6 mm (w). Color: Yellow-Green Group 145A. Anthocyanic pigments the color of Greyed-Red Group 180A have been observed.

*Peduncle.*—Surface: Generally smooth. Few stipitate glands on surface. Length: 50 to 55 mm average length. Color: Yellow-Green Group 145A. Anthocyanic pigments the color of Greyed-Red Group 180A observed. Strength: Strong.

*Borne.*—Singularly.

Flower bloom:

*Fragrance.*—Moderate floral fragrance.

*Duration.*—The blooms have a duration on the plant of approximately 10 days. After flowers have fully matured, petals do not fall cleanly away from plant.

*Size.*—On average, flower diameter is 65 mm when open. Depth of the flowers is 50 mm.

*Form.*—General shape: Double, with a high pointed center which is tightly closed. Shape of flower when viewed from the side: Upon opening, upper part: Flat. Upon opening, lower part: Convex. Open flower, upper part: Flat. Open flower, lower part: Flattened convex.

*Petalage.*—Average range is 26 to 30 petals under normal conditions with 6 petaloids.

Color:

*Upon opening, petals.*—Outermost petals: Outer side: Red-Purple Group 63 B to 63C. Inner Side: Red Group 55B. Innermost petals: Outer side: Red Group 63B to 63C with intonations of Red Group 49B at the basal zone. Inner Side: Red Group 55B with Red Group 49B at the basal zone.

*Upon opening, basal petal spots.*—Outermost petals: Outer side: Yellow Group 2B to 2C. Inner Side: Yellow Group 2B. Innermost petals: Outer side: Yellow Group 2B to 2C. Inner Side: Yellow Group 2B.

*After opening, petals.*—Outermost petals: Outer side: Red-Purple Group 63C. Inner Side: Red Group 55B. Innermost petals: Outer side: Red-Purple Group 63C. Inner Side: Red Group 55B.

*After opening, basal petal spots.*—Outermost petals: Outer Side: Yellow Group 2B to 2C. Inner Side: Yellow Group 2B. Innermost petals: Outer Side: Yellow Group 2B to 2C. Inner Side: Yellow Group 2B.

General tonality: On open flower Red Group 55B to Red-Purple Group 63C. No change in the general tonality at the end of the 10th day.

Petals:

*Petal reflex.*—Strongly.

*Margin.*—Entire with weak undulations.

*Shape.*—Apex is rounded. Base shape is acute.

*Size.*—35 mm (l)×30 mm (w).

*Texture.*—Smooth.

*Thickness.*—Thick.

*Arrangement.*—Formal.

Petaloids:

*Quantity.*—5 to 8.

*Color.*—Upper surface is Red Group 55B. Reverse side is Red-Purple Group 63C.

*Size.*—18 mm (l)×13 mm (w).

*Shape.*—Acute base shape. Rounded apex.

Reproductive organs:

*Pollen.*—None Observed.

*Anthers.*—Size: 2 mm in length. Color: Yellow-Orange 19A. Quantity: 124 (actual count).

*Filaments.*—Color: Orange-Red Group 31B to 31C. Length: 8 mm.

*Pistils.*—Length: 5 mm. Quantity: 41 (actual count).

*Stigmas.*—Superior in location relative to the length of the filaments and height of the anthers. Color: Orange-Red Group 35C.

*Styles.*—Color: Orange-Red Group 35C.

*Hips.*—None Observed in the field nursery in Jackson County, Oreg.

PLANT

Plant growth: Upright and bushy. When grown as a budded field grown plant on *Rosa multiflora* understock, the height of the plant is 60 to 100 cm and the average width is 75 cm.

Stems:

*Color.*—Young wood: Yellow-Green Group 144A. Older wood: Yellow-Green Group 144A.

*Surface texture.*—Young wood: Smooth. Older wood: Smooth.

Thorns:

*Incidence.*—5 thorns per 10 cm of stem.

*Size.*—Average length: 6 mm.

*Color.*—Greyed-Red Group 178A.

*Shape.*—Deeply concave.

Plant foliage: Normal number of leaflets on normal leaves in middle of the stem: 5 leaflets.

*Compound leaf size.*—115 mm (l)×70 mm (w).

*Color.*—Mature Foliage: Upper surface is Yellow-Green Group 144A to 146B. Lower surface is Yellow-Green Group 146C. Juvenile foliage: Upper surface is Yellow-Green Group 144A. Lower surface is Yellow-Green Group 146C. Anthocyanic pigments, the color of Greyed-Purple Group 187C broadly covering juvenile foliage.

Plant leaves and leaflets:

*Stipules.*—Size: 11 mm in length. Shape: Linear, slightly broad based with outward extending apecies. Quantity: 2 per compound leaf. Margins: Finely serrated with few stipitate glands. Color: Yellow-Green Group 144A. Anthocyanin: None observed.

*Petiole.*—Length: 30 mm. Color: Yellow-Green Group 144B. Observations: Thorns present on lower surface.

*Rachis.*—Length: 35 to 40 mm. Color: Yellow-Green Group 144B. Observations: Small prickles on the undersides, located mid-way between leaflets. Limited quantity of stipitate glands observed.

*Leaflet.*—Edge: Serrated. Size: Average size of the terminal leaflet on normal leaves is 55 mm in length by 40 mm wide. Shape: Generally ovate. Base shape is rounded. Apex is mucronate. Texture: Smooth. Thickness: Average. Arrangement: Odd pinnate. Venation: Reticulate. Glossiness: Glossy.

Disease resistance: Above average resistance to mildew, rust, black spot, and *Botrytis* under normal growing conditions in Jackson County, Oreg.

Cold hardiness: The variety 'POULpm002' has been found to be cold tolerant to USDA Cold Hardiness Zone 6.

We claim:

1. A new and distinct variety of rose plant of the hybrid tea rose class named 'Poulpm002', described and illustrated as a distinct and novel rose variety due to its abundant pink flowers, disease resistance, and extended period of bloom.

* * * * *

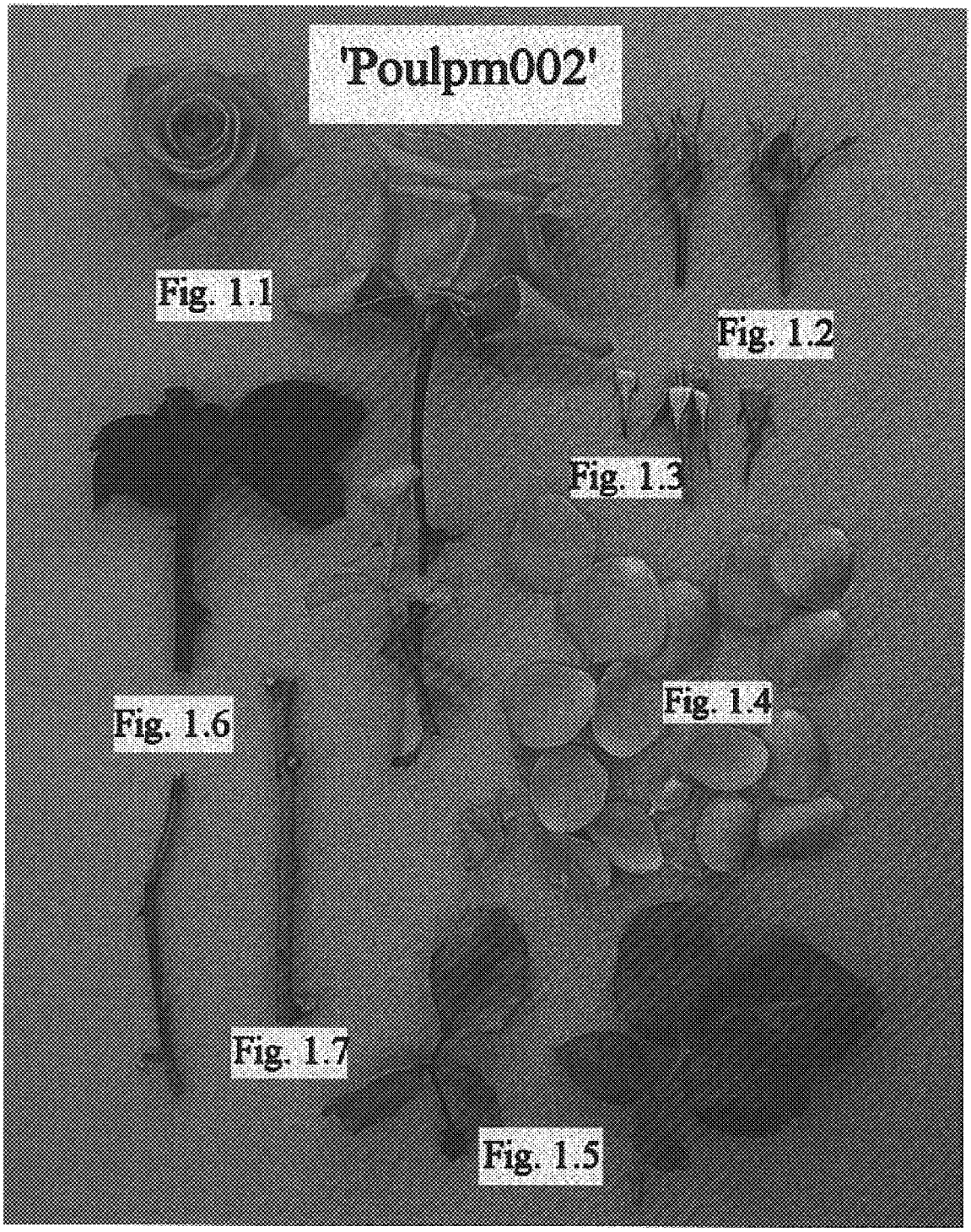
'Poulpm002'
Fig. 1.1
Fig. 1.2
Fig. 1.3
Fig. 1.4
Fig. 1.5
Fig. 1.6
Fig. 1.7